US 6,632,404 B1

(12) United States Patent
Freitag et al.

(10) Patent No.: US 6,632,404 B1
(45) Date of Patent: Oct. 14, 2003

(54) AUTOMATICALLY ACTUATED PARALLEL SAMPLE INJECTOR VALVE

(75) Inventors: J. Christopher Freitag, Santa Clara, CA (US); Miroslav Petro, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 23 days.

(21) Appl. No.: 09/631,442

(22) Filed: Aug. 2, 2000

(51) Int. Cl.[7] ............................................... B01L 11/00
(52) U.S. Cl. ................ 422/103; 73/863.72; 73/863.73; 137/247; 137/247.13; 422/88; 422/89; 422/90; 422/91; 422/92; 422/93; 422/70
(58) Field of Search .................. 73/863.72, 863.73; 422/99, 100, 102, 88–93, 70; 137/247, 247.13

(56) References Cited

U.S. PATENT DOCUMENTS

| 2,830,738 A | * | 4/1958 | Sorg et al. ............... 73/863.73 |
|---|---|---|---|
| 3,160,015 A | * | 12/1964 | Charlton et al. ......... 73/863.73 |
| 3,222,135 A | * | 12/1965 | Ashmead ..................... 422/103 |
| 3,298,786 A | * | 1/1967 | Hinsvark ..................... 436/127 |
| 3,570,540 A | * | 3/1971 | McInnes et al. ........ 137/625.48 |
| 3,915,652 A | * | 10/1975 | Natelson ...................... 422/65 |
| 3,933,165 A | * | 1/1976 | Budzak et al. .......... 137/625.48 |
| 4,022,065 A | | 5/1977 | Ramin et al. ................. 73/422 |
| 4,047,540 A | | 9/1977 | Orme et al. ................. 137/239 |
| 4,064,908 A | | 12/1977 | Loe ........................... 137/614.17 |
| 4,168,235 A | | 9/1979 | Guillemin et al. .......... 210/198 |
| 4,182,184 A | | 1/1980 | Bakalyar et al. ............. 73/422 |
| 4,580,759 A | | 4/1986 | Leaseburge et al. .......... 251/62 |
| 5,034,193 A | * | 7/1991 | Maroulis et al. ............. 422/89 |
| 5,205,845 A | | 4/1993 | Sacks et al. ................... 55/197 |
| 5,367,912 A | * | 11/1994 | Demachi .................. 73/863.73 |
| 5,390,552 A | * | 2/1995 | Demachi et al. ......... 73/863.73 |
| 5,449,064 A | | 9/1995 | Hogan et al. ............. 204/180.1 |
| 5,524,496 A | * | 6/1996 | Nagai et al. .............. 73/863.73 |
| 5,578,268 A | * | 11/1996 | Champseix et al. .......... 422/63 |
| 5,780,717 A | * | 7/1998 | Wise et al. ............... 73/864.81 |
| 5,803,117 A | | 9/1998 | Olsen et al. ............ 137/625.15 |
| 5,961,925 A | | 10/1999 | Ruediger et al. .............. 422/99 |
| 6,012,487 A | * | 1/2000 | Hauck .................... 137/625.11 |
| 6,149,882 A | * | 11/2000 | Guan et al. .................. 422/211 |
| 6,296,749 B1 | * | 10/2001 | Balch et al. ................. 204/452 |
| 6,318,157 B1 | * | 11/2001 | Corso et al. ................ 73/61.52 |

FOREIGN PATENT DOCUMENTS

WO      WO 00/26662      * 5/2000

OTHER PUBLICATIONS

PCT International Publication No: WO 99/51980, Publication Date Oct. 14, 1999.
PCT International Publication No: WO 00/09255, Publication Date Feb. 24, 2000.

* cited by examiner

*Primary Examiner*—Jill Warden
*Assistant Examiner*—Elizabeth Quan
(74) *Attorney, Agent, or Firm*—Senniger, Powers, Leavitt & Roedel

(57) ABSTRACT

A sample injector valve capable of introducing multiple samples of material into multiple liquid or gas streams is provided. Such a valve is particularly useful for injecting multiple samples under pressure into a combinatorial chemistry system with moving streams of fluid, such as a parallel pressure reactor or a rapid flow analysis system using multi-channel or parallel chromatography and related techniques. The valve is further capable of functioning on a small scale with automatic sampling equipment.

28 Claims, 15 Drawing Sheets

POSITION 1

POSITION 2

POSITION 1

POSITION 2

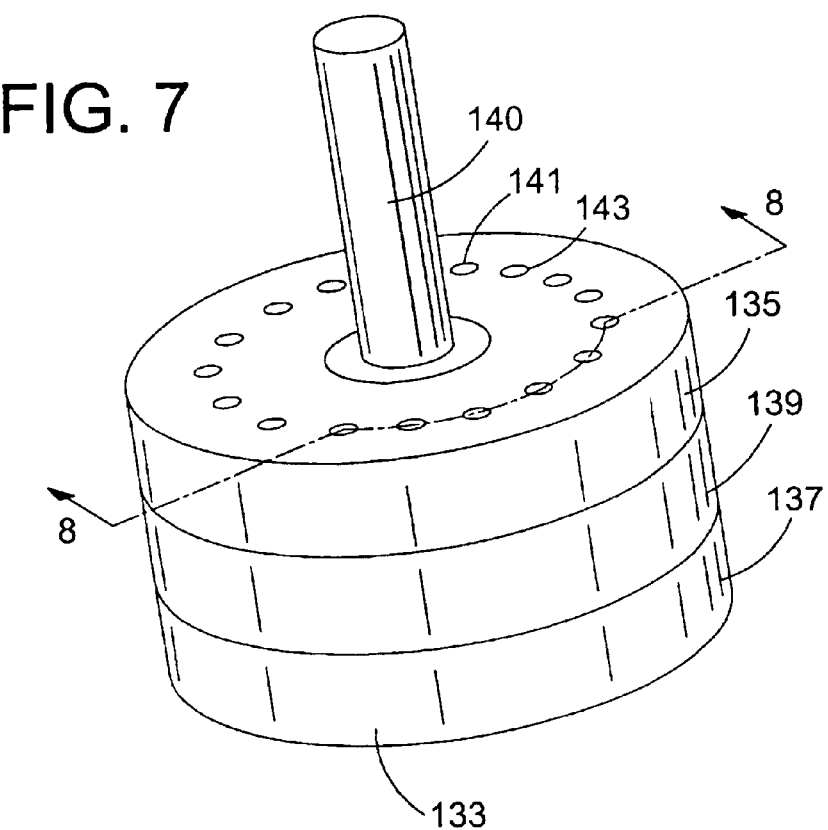
FIG. 7
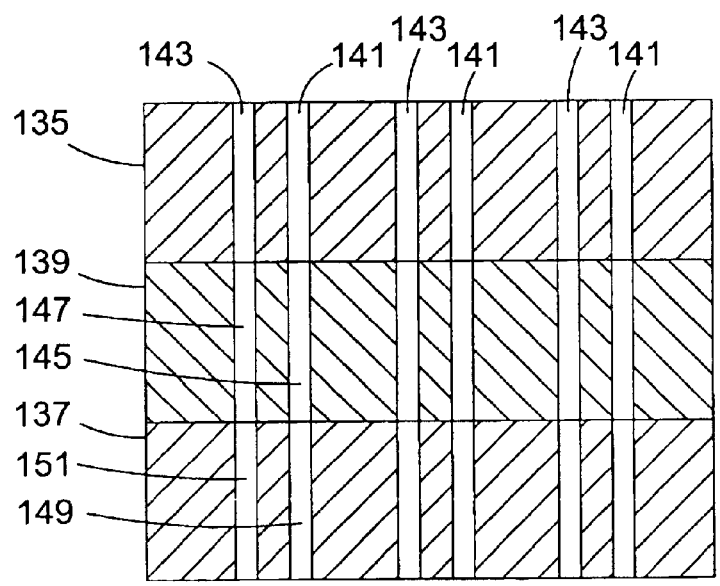
FIG. 8A (POSITION 1)

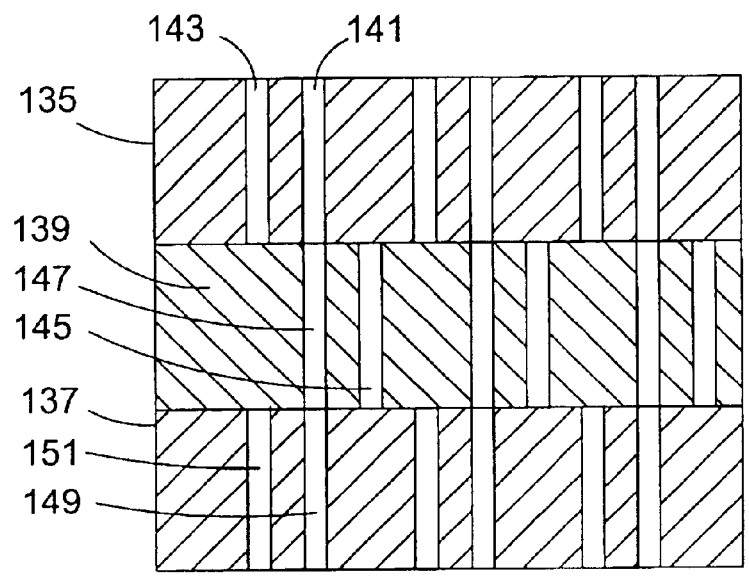
FIG. 8B (POSITION 2)
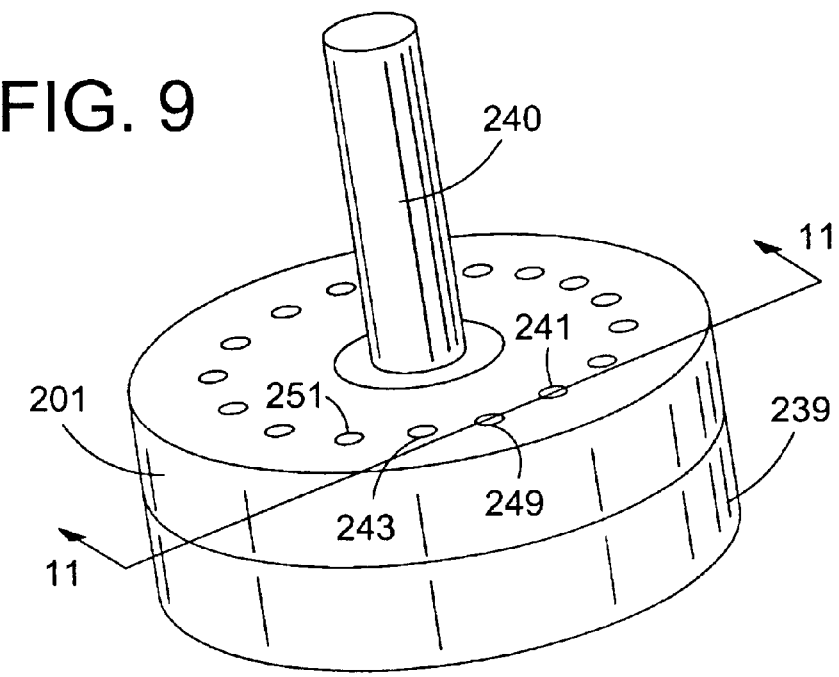
FIG. 9

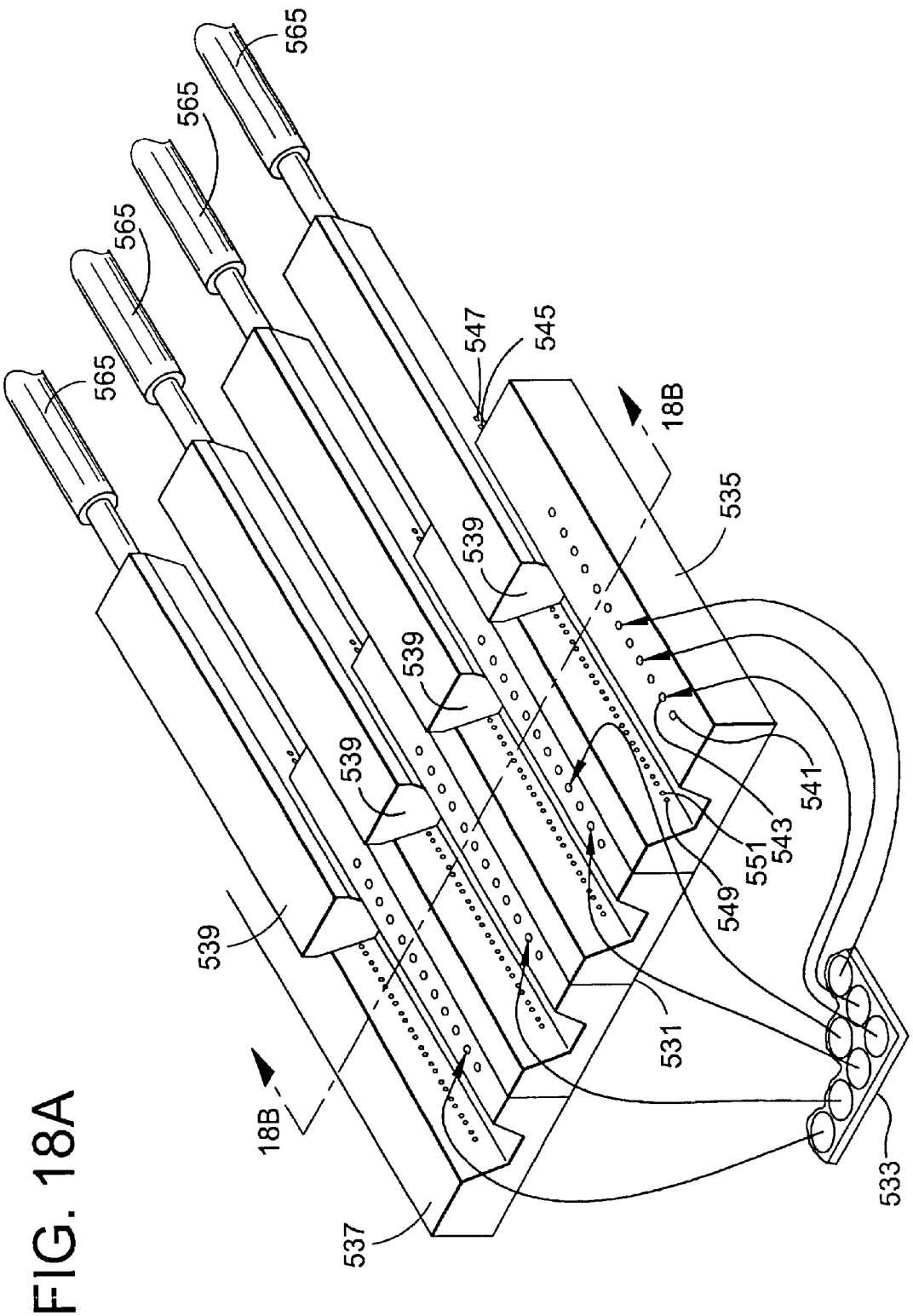

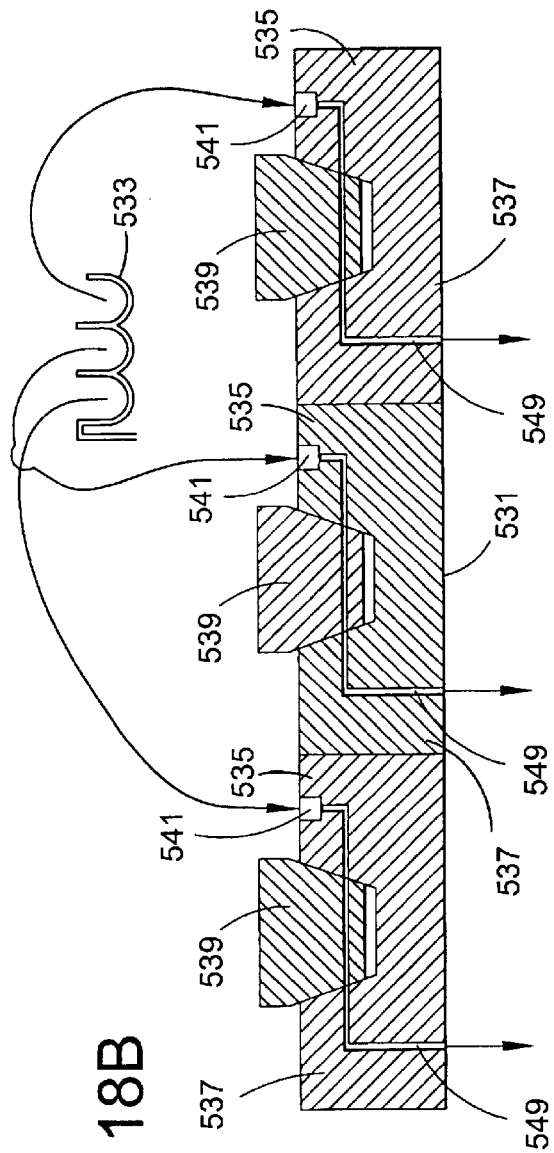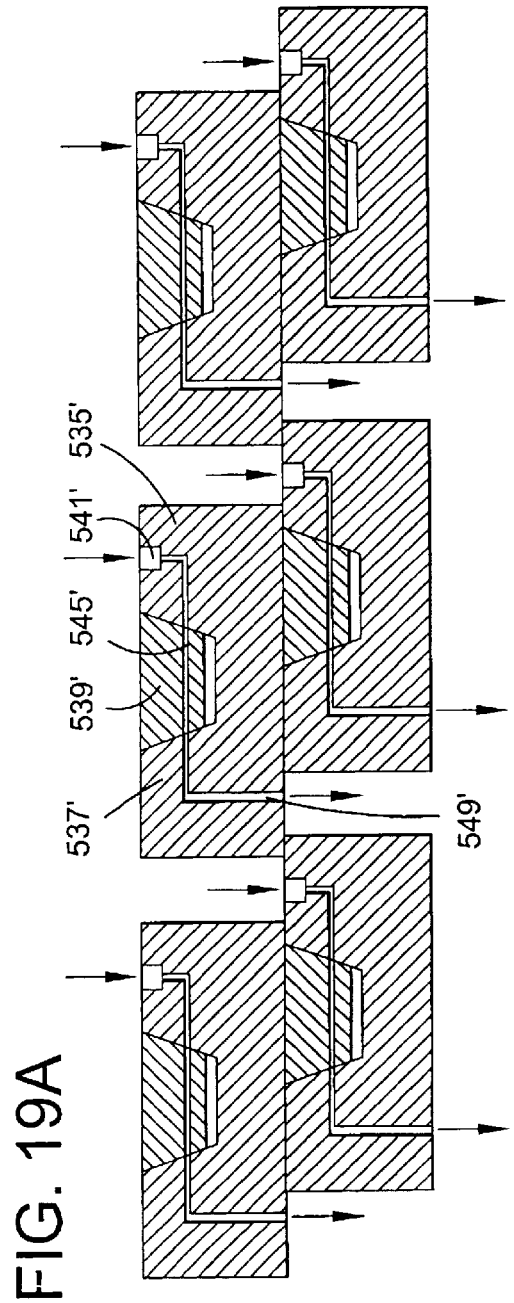

US 6,632,404 B1

AUTOMATICALLY ACTUATED PARALLEL SAMPLE INJECTOR VALVE

BACKGROUND OF THE INVENTION

The present invention generally relates to a sample injector valve capable of introducing multiple samples of material into multiple liquid or gas streams. Such a valve is particularly useful for injecting multiple samples under pressure into a combinatorial chemistry system with moving streams of fluid, such as a parallel pressure reactor or a rapid flow analysis system using multi-channel or parallel chromatography and related techniques.

In combinatorial chemistry, a large number of candidate materials are created from a relatively small set of precursors and subsequently evaluated for suitability for a particular application. As currently practiced, combinatorial chemistry permits scientists to systematically explore the influence of structural variations in candidates by dramatically accelerating the rates at which they are created and evaluated. Compared to traditional discovery methods, combinatorial methods sharply reduce the costs associated with preparing and screening each candidate.

Combinatorial chemistry systems generally include apparatus for high throughput material synthesis as well as material evaluation. For example, WO 00/09255, incorporated herein by reference, discloses a parallel pressure reactor with methods and apparatus for synthesizing, screening and characterizing combinatorial libraries. Further, combinatorial systems may include flow characterization methods such as liquid chromatography or flow-injection analysis for the evaluation of a combinatorial library. Liquid chromatography and flow-injection analysis comprise methods of injecting a sample into a mobile phase of fluid to detect specific properties of the sample. For example, in liquid chromatography, a sample is injected into a mobile phase and passed through a chromatographic column. The chromatographic column then acts to separate one or more components of the sample by elution and the separated components are analyzed with a flow-through detector.

Traditional flow characterization systems have been designed primarily with respect to sample type and quality of information. However, in applying a traditional flow analysis apparatus in a combinatorial chemistry system, overall sample throughput is of a concern. Recent work directed at improving the efficiency of characterization and analysis for traditional flow analysis systems has focused on the total amount of analysis time required from sample preparation through detection. For example, Yoshida et al., U.S. Pat. No. 5,783,450 discloses a liquid chromatography system wherein parallel sample preparation reduces overall analysis time. WO 99/51980, incorporated herein by reference, discloses a method and system to increase sample throughput for the rapid characterization of polymers using a high pressure liquid chromatography apparatus.

However, the decrease in analysis time has not heretofore included an increase in the rate of delivery of samples for analysis. Even the aforementioned, improved flow analysis systems use conventional rotary sample injector valves wherein samples are loaded into sample loops for series injection into a mobile phase. Thus, the size of these conventional rotary valves limits the scale and number of channels that can be filled with samples. Such rotary injector valves can only inject one sample at a time into the mobile phase, placing further constraints on sample throughput. For example, WO 99/51980 discloses using different combinations of analysis steps both in series and in parallel to decrease the overall time spent on a sample but the systems disclosed use only a single rotary sample injector valve that can accommodate only one mobile phase. Thus, there is presently a need for a sample injector valve that can simultaneously inject multiple samples into multiple streams of fluid to further increase sample throughput in a combinatorial chemistry system.

SUMMARY OF THE INVENTION

Among the several objects and features of the present invention may be noted the provision of a sample injector valve for use in the rapid parallel injection of samples of material into a combinatorial chemistry system; the provision of such a valve which is of unitary, compact construction; the provision of such a valve which injects multiple samples with a single actuation; the provision of such a valve which cooperates with conventional automated injection apparatus and the provision of such a valve which augments combinatorial chemistry equipment.

Briefly, apparatus of this invention is a sample injector valve comprising a block and a shuttle for use in injecting samples into a combinatorial chemistry system. The block includes carrier fluid entry passages and carrier fluid exit passages. The carrier fluid entry passages are adapted for connection to a source of pressurized carrier fluid for urging carrier fluid to flow through the valve. The block further includes sample entry passages and sample vent passages. The shuttle is slidingly received in substantially sealing relationship to the block. The shuttle has transfer passages therein having sample collection volumes. An actuator is operatively connected to the shuttle for moving the shuttle in the valve between a first position in which samples of material to be analyzed can be collected in the shuttle and a second position in which collected samples can be fed into said carrier fluid exit passages for delivery to a combinatorial chemistry system. In the first position, at least some of the transfer passages of the shuttle are substantially in registration with respective ones of the sample entry passages and sample vent passages of the block for receiving a volume of sample material substantially equal to the sample collection volume of the transfer passage. In the second position, at least some of the transfer passages of the shuttle are substantially in registration with respective ones of said carrier fluid entry and exit passages for substantially simultaneous delivery of the multiple collected sample in the transfer passage into said carrier fluid exit passage under pressure of the carrier fluid.

Other objects and features of the present invention will be in part apparent and in part pointed out hereinafter.

BRIEF DESCRIPTION OF THE DRAWINGS

FIG. 7 is a perspective of a fifth, rotary embodiment of the parallel sample injector valve;

FIG. 8A is a section of the rotary embodiment taken along the line 8—8 of FIG. 7 with the sample transfer shuttle in a first position;

FIG. 8B is the section of FIG. 8A, but showing the sample transfer shuttle in a second position;

FIG. 9 is a perspective of a sixth, rotary embodiment of the parallel sample injector valve;

FIG. 18A is a perspective of an embodiment of the present invention incorporating multiple parallel sample injector valves of the present invention into a two-dimensional array;

FIG. 18B is a vertical cross section taken along the line 18B—18B of FIG. 18A with the sample transfer shuttles out of a normal operating position to show detail;

Corresponding reference characters indicate corresponding parts throughout the several views of the drawings.

DETAILED DESCRIPTION OF THE PREFERRED EMBODIMENTS

The present invention provides an automatically actuated parallel sample injector valve capable of simultaneously introducing multiple samples into multiple liquid or gas streams. Such a valve is particularly useful for injecting multiple samples under pressure into a combinatorial chemistry system with moving streams of fluid, such as a parallel pressure reactor or a rapid flow analysis system using multi-channel or parallel chromatography and related techniques. For purposes of this invention, the term "combinatorial chemistry system" is defined to include any combinatorial chemistry or high throughput application utilizing moving streams of fluid including chemical synthesis applications such as a parallel pressure reactor and combinatorial library evaluation applications such as a flow characterization analysis system (e.g., gas chromatography, liquid chromatography or flow detection). Although the present invention is described throughout the specification and shown in FIG. 1 as operating in a parallel liquid chromatography analysis system, it is important to note that the valve can be employed in any system wherein multiple samples are simultaneously injected into moving streams of fluid including combinatorial chemical synthesis or evaluation applications.

Figure 1:
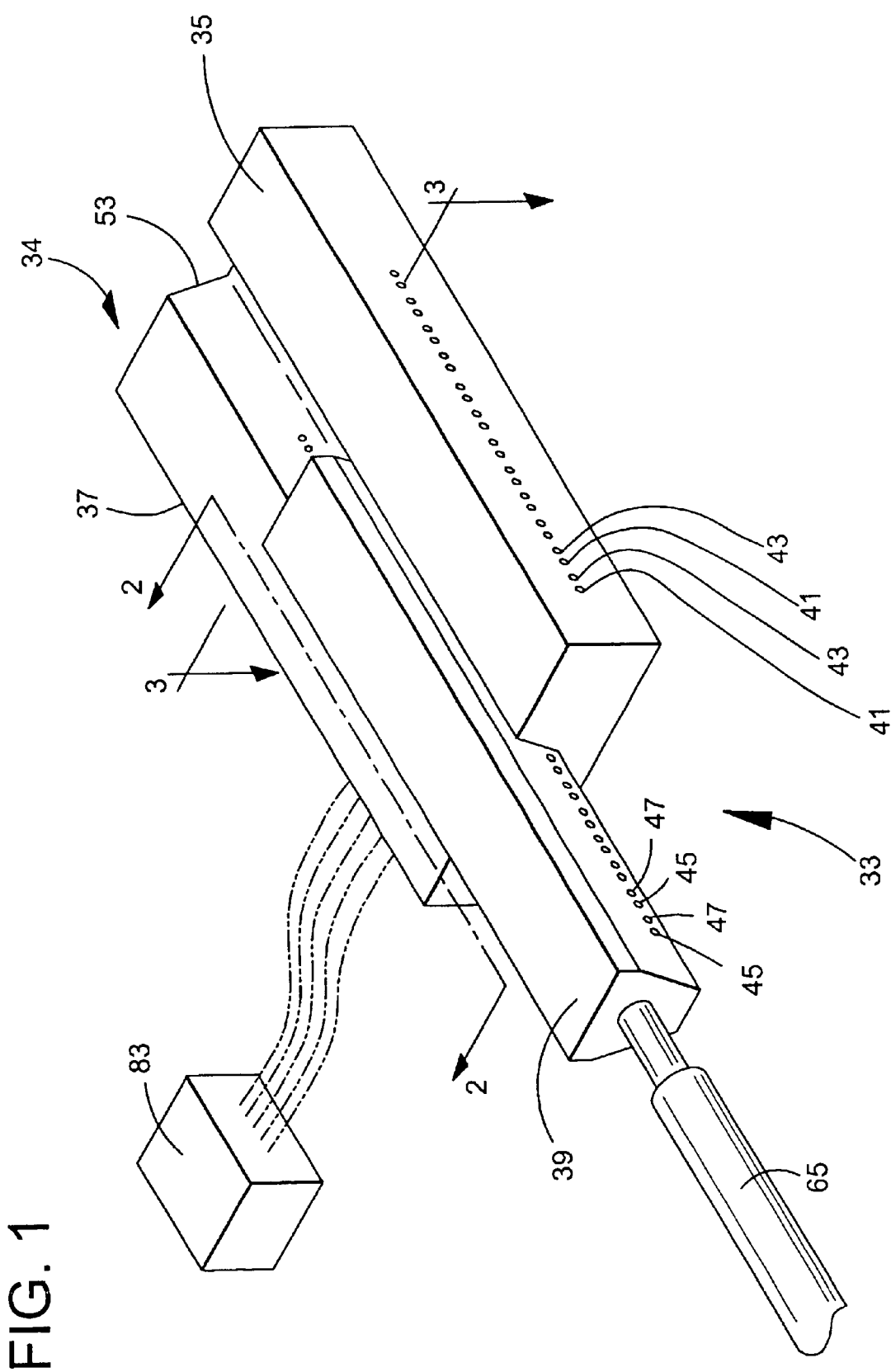
FIG. 1 is a perspective view of a parallel sample injector valve of a first embodiment, the sample transfer shuttle being offset from its normal operating position for purposes of illustration.

Referring now to the drawings, an automatically actuated parallel sample injector valve of the present invention is generally indicated at 33 in FIG. 1. The valve 33 is particularly useful for simultaneously injecting multiple samples of material into a combinatorial chemistry synthesis or flow analysis apparatus 83. For example, the valve is useful in a parallel liquid chromatography system wherein multiple samples are simultaneously injected into a carrier fluid mobile phase for separation and analysis. In such an application, the valve can be advantageously designed to inject, for example, from 8 to 12 material samples into a pressurized carrier fluid mobile phase on 9 mm spacings to facilitate the use of standard robot autosamplers known in the art of liquid chromatography.

Figure 1A:
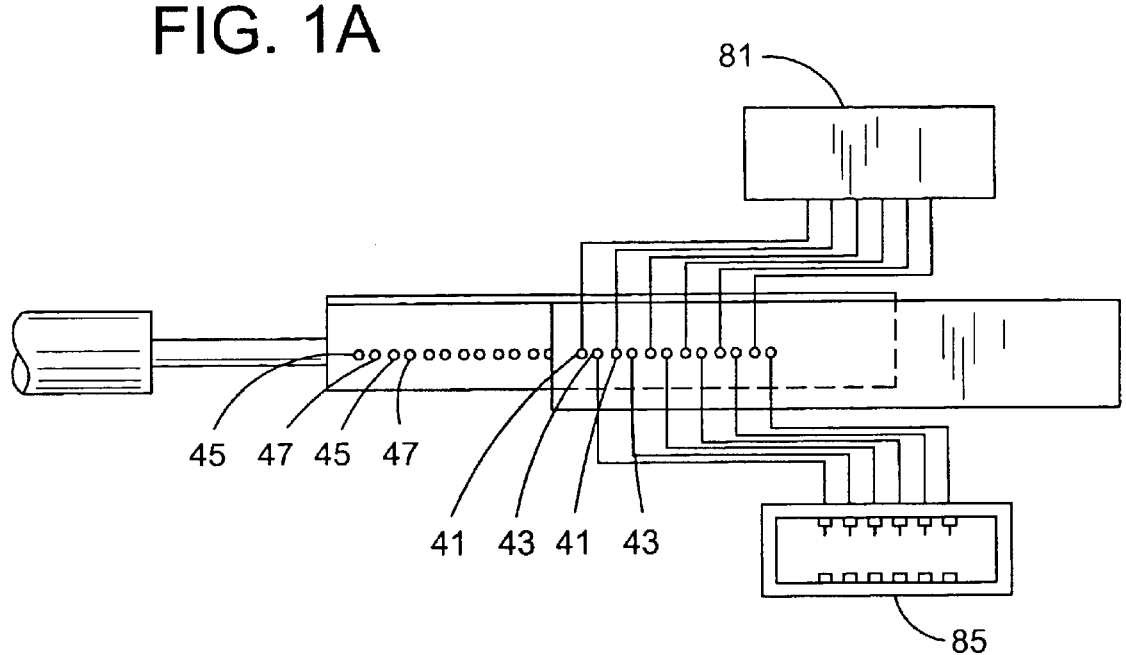
FIG. 1A is an enlarged schematic side view of the valve showing preferred connections of the parallel sample injector valve to a carrier fluid source and an automatic sampler.
Figure 2:
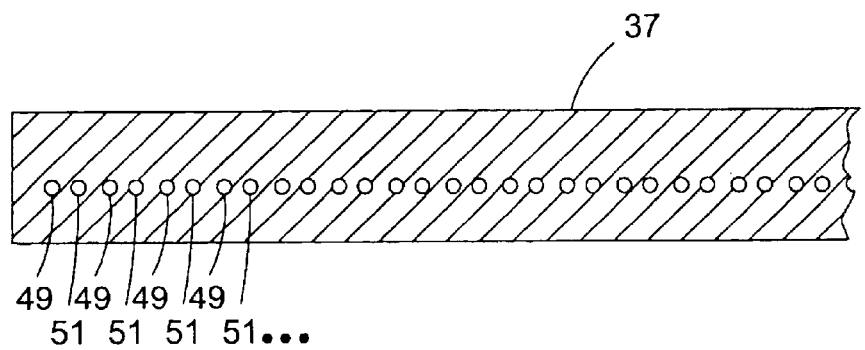
FIG. 2 is a fragmentary section taken along the line 2—2 of FIG. 1.

As shown in FIG. 1, the valve 33 comprises a block (generally indicated at 34) including a carrier fluid entry block member 35, a carrier fluid exit block member 37, and a sample transfer shuttle 39. The shuttle 39 has been extended out from its normal operating position between the blocks 35, 37 in FIG. 1 to illustrate its construction. The carrier fluid entry block member 35 has carrier fluid entry passages 41, and sample entry passages 43 therein. The carrier fluid entry passages 41 are adapted for connection to a source of pressurized carrier fluid 81 to flow through the valve as shown in FIG. 1A. Preferably, the sample entry passages 43 are adapted (as by their spacing) to accommodate the use of a commercially available robot auto-sampler 85 (FIG. 1A) such as a CAVRO RSP9000 available from CAVRO Scientific Instruments, Inc. of Sunnyvale, Calif. The sample transfer shuttle 39 has carrier fluid transfer passages 45, and sample collection passages 47 therein. Each of the sample collection passages 47 are sized and shaped to define a sample collection volume corresponding to the desired volume of sample to be analyzed by the flow characterization system. Referring briefly to FIG. 2, the carrier fluid exit block member 37 includes carrier fluid exit passages 49 and sample vent passages 51. The carrier fluid exit passages 49 are adapted for connection to a flow analysis or a combinatorial synthesis apparatus 83 such as a high pressure liquid chromatography apparatus as disclosed in WO 99/51980 or a parallel pressure reactor as disclosed in WO 00/09255, both of which are herein incorporated by reference.

Referring again to FIG. 1, the figure shows the carrier fluid entry block member 35 and the carrier fluid exit block member 37 formed as the single piece block 34; however, it is contemplated that the carrier fluid entry block member 35, the sample transfer shuttle 39 and the carrier fluid exit block member 37 may comprise three separate bodies. In the first embodiment, the carrier fluid entry block member 35 and the carrier fluid exit block member 37 are partially spaced apart to define a channel 53 separating the carrier fluid entry passages 41 and sample entry passages 43 of the carrier fluid entry block member 35 from the carrier fluid exit passages 49 and the sample vent passages 51 of the carrier fluid exit block member 37. The sample transfer shuttle 39 is slidingly received in the channel 53 in substantially sealing relationship to the carrier fluid entry block member 35 and carrier fluid exit block member 37.

As is generally known by those skilled in the art, the choice of manufacturing materials and manufacturing tolerances relative to the fluid viscosity, surface tension and the fluid pressure in a given application will be essential in providing for a substantially sealing relationship between the sample transfer shuttle 39 and the carrier fluid entry block member 35 and carrier fluid exit block member 37. Therefore, it is contemplated that several methods of sealing two bodies apparent to one skilled in the art are suitable in manufacturing the present invention. For example, the carrier fluid entry and exit block members 35, 37 and the sample transfer shuttle 39 may all comprise hard surfaces (e.g. stainless steel) wherein the sealing relationship is established by polishing the opposing surfaces of the members and the shuttle to a mirror-like finish, preferably with less than about a 4 to about a 16 microinch root-mean-square feature height. Alternatively, one of the opposing surfaces, of either the carrier fluid entry and exit block members 35, 37 or of the sample transfer shuttle 39, may be constructed of a soft material such as an elastomer or a polymer while the other opposing surface is constructed of a hard material, e.g., stainless steel. The substantially sealing relationship is then achieved by conforming the elastomer material surface against the hard material surface without exceeding the limits of the particular elastomer. Preferably, any sealing arrangement is complemented by a spring (not shown). As is apparent to one skilled in the art, the spring must be pre-loaded with a sufficient force to withstand the pressure of the fluid flowing against the sealing surface. While the pre-loaded force assists in maintaining a sealing relationship, it also increases the amount of friction between the sealing surfaces. Therefore, the manufacturing materials and surface finishes of the opposing sealing surfaces are critical in determining the amount of friction generated and the corresponding wear within the parallel sample valve.

In a preferred embodiment, sealing is achieved using a trapezoidal geometry for the sample transfer shuttle 39. As shown in FIG. 1, the sample transfer shuttle 39 and the carrier fluid entry and exit blocks 35, 37 are formed of opposing trapezoidal geometries such that the sample transfer shuttle 39 is arranged to form a partial mating wedge with the carrier fluid entry block member 35 and the carrier fluid exit block member 37. A force is then applied to the sample transfer shuttle 39 by a pre-loaded spring (not shown) to maintain a substantial sealing relationship with the carrier fluid entry block member 35 and the carrier fluid exit block member 37.

Figure 3A:
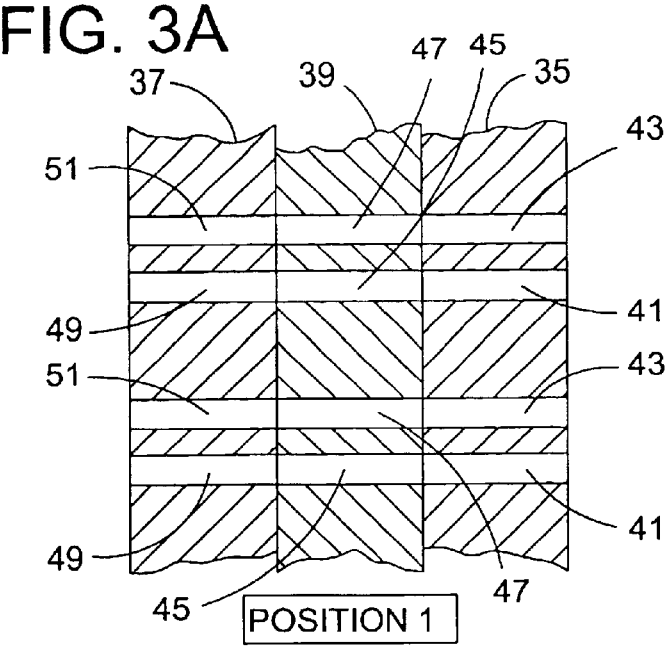
FIG. 3A is a section taken along the line 3—3 of FIG. 1 with a sample transfer shuttle of the valve in a first position.
Figure 3B:
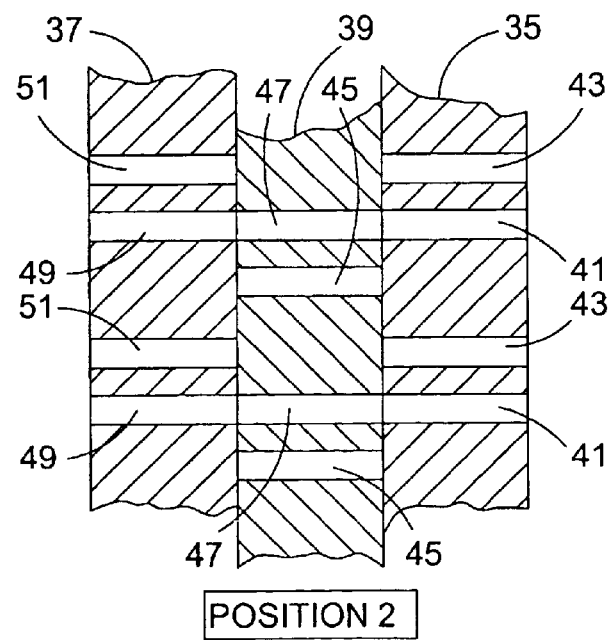
FIG. 3B is the section of FIG. 3A, but showing the sample transfer shuttle in a second position.

The sample injector valve operates by moving the sample transfer shuttle 39 between a first position as shown in FIG. 3A and a second position as shown in FIG. 3B. Referring again to FIG. 1, the sample transfer shuttle 39 is moved by an actuator 65 operatively connected to the sample transfer shuttle. The actuator 65 has been extended out from its normal operating position along with the sample transfer shuttle 39 in FIG. 1 to illustrate its construction. The actuator can be of any suitable type generally known in the art. For example, the actuator may be a pneumatic or hydraulic cylinder including those that operate with or without closed loop control. Further, the actuator may also be electric, comprising either a linear servo motor or a linear stepper motor. Still further, the actuator may be an electromagnetic solenoid or rotary with a leadscrew including a servo, stepper or brush motor.

Referring now to FIG. 3A, in the first position of the sample transfer shuttle 39, the sample collection passages 47 are substantially in registration with respective ones of the sample entry passages 43 of the carrier fluid entry block member 35 and sample vent passages 51 of the carrier fluid exit block member 37. The carrier fluid transfer passages 45 are in substantial registration with respective ones of the carrier fluid entry passages 41 of the carrier fluid entry block member 35 and carrier fluid exit passages 49 of the carrier fluid exit block member 37.

In operation of the valve, a volume of sample is allowed to collect in the sample collection passages 47 when the sample transfer shuttle 39 is in the first position. As above, each of the sample collection passages 47 are sized and shaped to define a sample collection volume corresponding to the desired sample volume for the particular combinatorial chemistry application being employed. The sample transfer shuttle 39 is then moved to a second position as shown in FIG. 3B by the actuator. In the second position of the sample transfer shuttle 39, the sample collection passages 47 are substantially in registration with respective ones of the carrier fluid entry passages 41 and carrier fluid exit passages 49. The volume of collected sample in the sample collection passages 47 is delivered into the carrier fluid exit passages 49 under pressure of the carrier fluid.

Figure 4A:
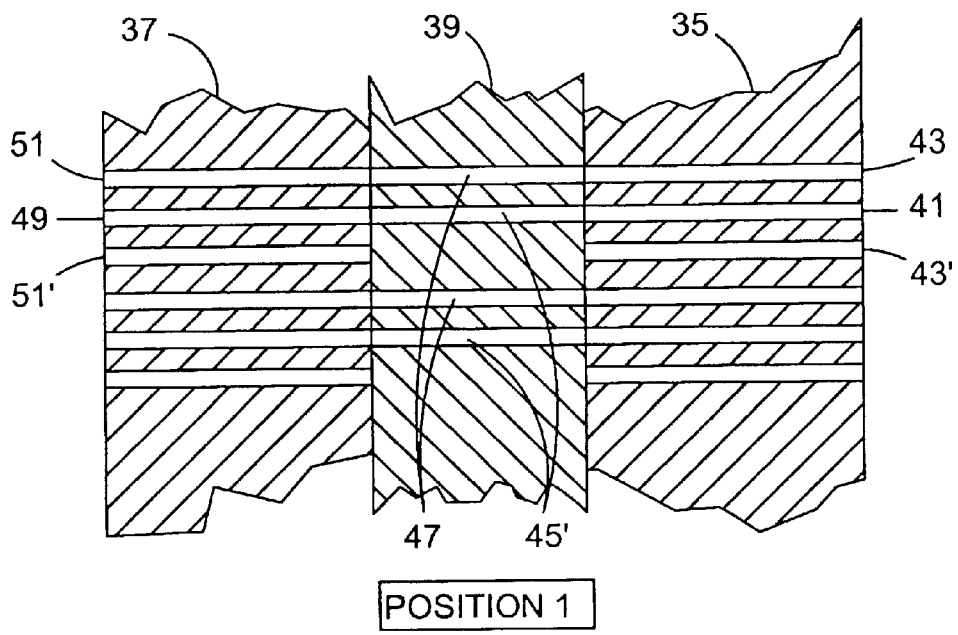
FIG. 4A is a horizontal cross section similar to FIG. 3A, but showing a second embodiment of the parallel sample injector valve with a sample transfer shuttle of the valve in a first position.
Figure 4B:
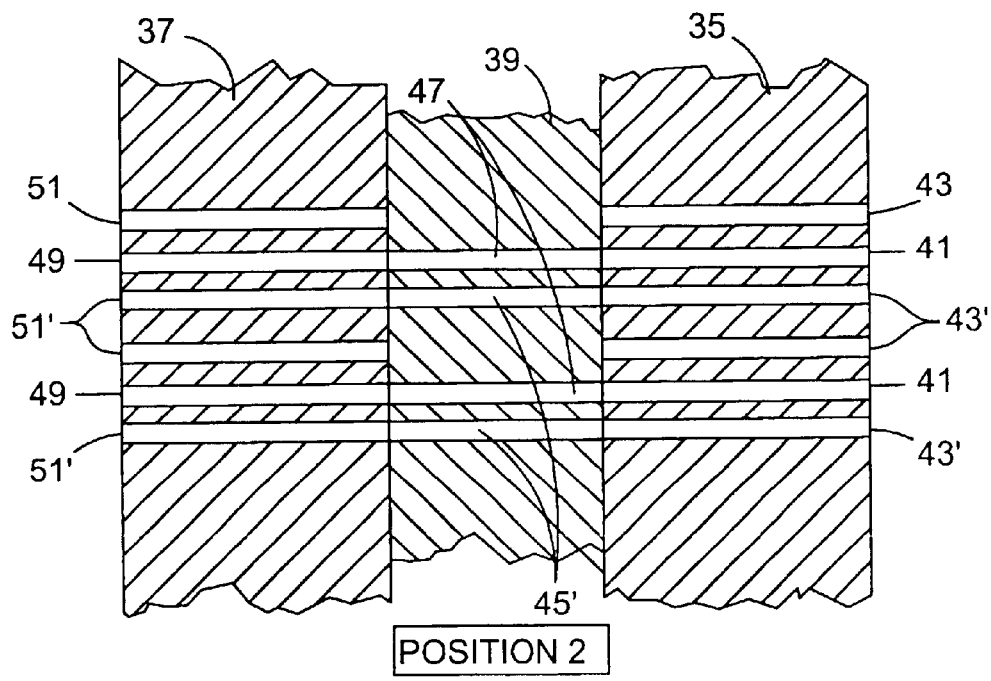
FIG. 4B is the section of FIG. 4A, but showing the sample transfer shuttle in a second position.

In a second embodiment, the valve can be operated in a "load-load" configuration wherein one set of samples is collected in sample collection passages while another set of samples is delivered to the carrier fluid exit stream. An example of such a "load-load" configuration is shown in FIGS. 4A and 4B. Referring now to FIG. 4A, the valve is substantially the same as the sample injector valve described above, except that the carrier fluid entry block member 35 further includes other sample entry passages 43', the carrier fluid exit block member 37 further includes other sample vent passages 51' and the sample transfer shuttle further includes passages 45' which functioned as carrier fluid transfer passages in the first embodiment. The passages 45' are sized and shaped to define a sample collection volume for collecting and delivering samples to the carrier fluid stream. It is contemplated that the passages 45' and the sample collection passages 47 may be sized and shaped to define equivalent sample collection volumes, or such sample collection volumes may be sized and shaped independently to define different sample collection volumes depending on the sampling protocol to be employed.

The operation of the valve is as described for the first embodiment above wherein a volume of sample is allowed to collect in the sample collection passages 47 when the sample transfer shuttle 39 is in the first position. When the actuator moves the sample transfer shuttle 39 to a second position as shown in FIG. 4B, the sample collection passages 47 are substantially in registration with the carrier fluid entry passages 41 of the carrier fluid entry block member 35 and the carrier fluid exit passages 49 of the carrier fluid exit block member 37. The volume of sample collected in the sample collection passages 47 is delivered to the carrier fluid stream and carried through the carrier fluid exit passages 49 under pressure of the carrier fluid. However, the operation of the valve is distinguished from the first embodiment in that, in the second position of the sample transfer shuttle 39, the passages 45' are arranged to collect a volume of sample from the other sample entry passages 43'. In other words, in the second position of the sample transfer shuttle 39 (FIG. 4B), the passages 45' are substantially in registration with the other sample entry passages 43' of the carrier fluid entry block member 35 and the other sample vent passages 51' of the carrier fluid exit block member 37. Thus, a second set of samples can be collected in the passages 45' while the first set of samples in the sample collection passages 47 is delivered to the carrier fluid exit passages 49. When the sample transfer shuttle 39 is returned to the first position (FIG. 4A), the second set of samples collected in the passages 45' is delivered to the carrier fluid exit passages 49 under pressure of the carrier fluid.

Other embodiments are contemplated within the scope of the present invention wherein the sample injector valve can operate while maintaining a constant pressure in the carrier fluid exit stream. Maintaining constant pressure may be important in applications where a pressure drop or a pressure spike could disrupt the downstream flow analysis system. Such pressure drops can occur when the sample transfer shuttle is switched between positions or when a viscous sample is injected into the carrier fluid mobile phase.

Figure 5:
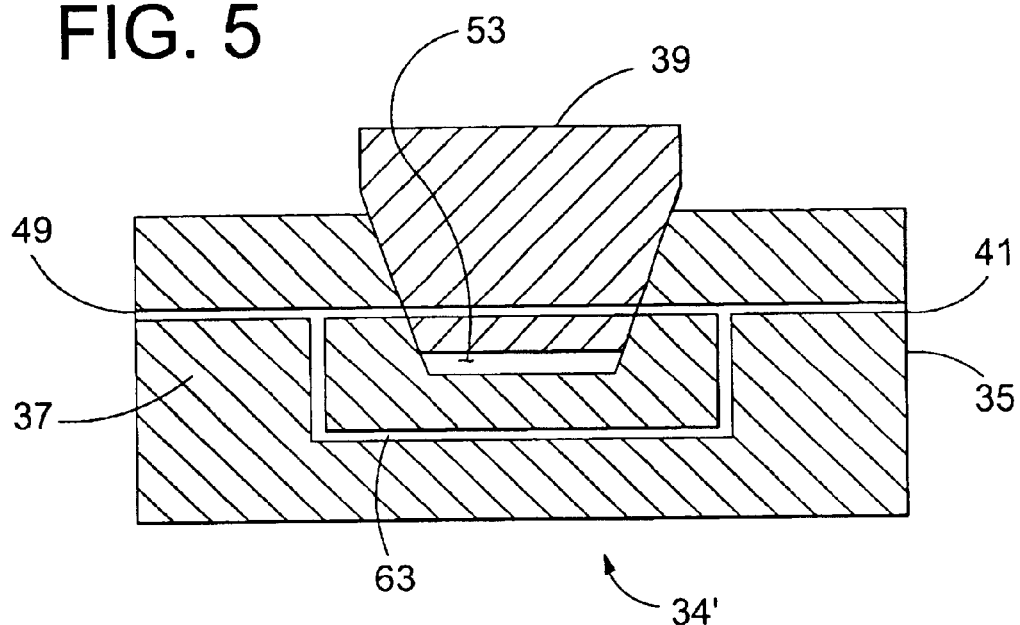
FIG. 5 is a vertical cross section of a third embodiment of the parallel sample injector valve.

An example of a third embodiment able to maintain a more nearly constant pressure in the carrier fluid exit stream is shown in FIG. 5. Referring to the figure, the sample injector valve is as described above wherein the carrier fluid entry block member 35 and the carrier fluid exit block member 37 are formed as the single piece block 34'. The single piece block 34' is distinguished from the valve 33 of the first embodiment in that it includes a carrier fluid bypass passage 63 providing open fluid communication between each carrier fluid entry passage 41 and the corresponding carrier fluid exit passage 49. It is contemplated by the present invention that the valve 33 may include any combination of carrier fluid bypass passages 63 to correspond with the carrier fluid entry passages 41 and carrier fluid exit passages 49. For example, there may be only one carrier fluid bypass passage 63 in fluid communication with all carrier fluid entry passages 41 and all carrier fluid exit passages 49, there may be a single carrier fluid bypass passage 63 corresponding to each carrier fluid entry passage 41 and carrier fluid exit passage 49 (as is shown), or any combination of multiple carrier fluid entry passages 41 and carrier fluid exit passages 49 corresponding to each carrier fluid bypass passage 63. The carrier fluid bypass passages 63 maintain a substantially continuous flow of carrier fluid between the carrier fluid entry passages 41 and the carrier fluid exit passages 49 such that the pressure of carrier fluid flowing through the carrier fluid exit passages 49 to the flow analysis or combinatorial synthesis apparatus 83 as shown in FIG. 1 is substantially constant.

Figure 6:
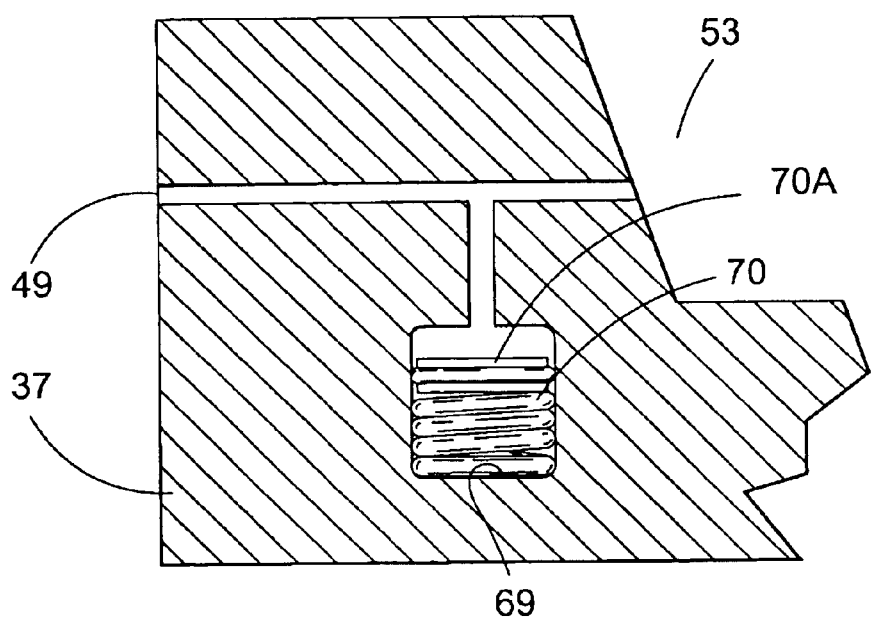
FIG. 6 is an enlarged, fragmentary vertical cross section of a fourth embodiment of the parallel sample injector valve.

A fourth embodiment, illustrated in FIG. 6, also maintains a substantially constant pressure in the carrier fluid exit stream. Referring to FIG. 6, the sample injector valve may be substantially the same as any of the embodiments as described above. However, in the fourth embodiment, the carrier fluid exit block member 37 further includes an accumulation chamber 69. The accumulation chamber 69 operates such that in normal flow of the carrier fluid through the carrier fluid exit passages 49, carrier fluid is allowed to accumulate in the chamber. The carrier fluid under pressure depresses a spring 70 in the accumulation chamber 69. The spring 70 has a head 70a which seals the upper portion of the accumulation chamber 69 from the lower portion which accommodates the spring. Further, the accumulation chamber 69 may be vented such that a vacuum is not created by the operation of the spring 70. When a decrease in carrier fluid pressure is encountered in the carrier fluid exit passage 49, carrier fluid from the accumulation chamber 69 is ejected by the spring 70 from the accumulation chamber 69 into the carrier fluid exit passages 49 to compensate for the decrease in carrier fluid pressure. Thus, a substantially constant pressure is maintained in the carrier fluid exit stream flowing to the analyzing or combinatorial synthesis apparatus 83 as shown in FIG. 1. Pressure regulation mechanisms other than a spring may be employed. For instance, it is contemplated that the previously described embodiment may comprise an accumulation chamber 69 including a bladder (not shown) that is filled with a compressible fluid and attached to a reservoir. Thus, when a decrease in carrier fluid pressure is encountered in the carrier fluid exit passage 49, carrier fluid from the accumulation chamber 69 is ejected by the compressible fluid expanding the bladder to maintain a substantially constant pressure in the carrier fluid exit stream.

A sample injector valve of the present invention can also be of rotary design. Rather than having a shuttle which operates in a linear fashion, the shuttle can be sized and shaped for rotary motion relative to the first and second block members. A fifth embodiment of the parallel sample injector valve having a rotary motion shuttle is shown in FIG. 7. Referring to the figure, the valve is analogous to the embodiments defined above wherein the valve 133 comprises a carrier fluid entry block member 135, a carrier fluid exit block member 137 and a sample transfer shuttle 139. The valve is operated by a rotary actuator (not shown) which operates on a shaft 140 connected to the sample transfer shuttle 139. The sample transfer shuttle 139 is sandwiched between the carrier fluid entry block member 135 and the carrier fluid exit block member 137. Although not necessarily formed as a single piece, the carrier fluid entry block member 135 and carrier fluid exit block member 137 constitute the "block" in the fifth embodiment. Like the linear embodiments described above, the carrier fluid entry block member 135 includes carrier fluid entry passages 141 and sample entry passages 143. Referring now to FIG. 8A, the sample transfer shuttle 139 includes carrier fluid transfer passages 145 and sample collection passages 147. The sample collection passages are sized and shaped to define a sample collection volume. The carrier fluid exit block member 137 includes carrier fluid exit passages 149 and sample vent passages 151.

In the first position of the sample transfer shuttle 139 (FIG. 8A), the sample collection passages 147 are substantially in registration with respective ones of the sample entry passages 143 of the carrier fluid entry block member 135 and the sample vent passages 151 of the carrier fluid exit block member 137. The carrier fluid transfer passages 145 are in substantial registration with respective ones of the carrier fluid entry passages 141 of the carrier fluid entry block member 135 and the carrier fluid exit passages 149 of the carrier fluid exit block member 137.

In operation of the valve, a volume of sample is allowed to collect in the sample collection passages 147 when the sample transfer shuttle 139 is in the first position. The sample transfer shuttle is then moved to a second position, as shown in FIG. 8B, by the actuator. In the second position of the sample transfer shuttle 139, the sample collection passages 147 are substantially in registration with respective ones of the carrier fluid entry passages 141 and the carrier fluid exit passages 149. The volume of sample collected in the sample collection passages 147 is delivered into the carrier fluid exit passages 149 under pressure of the carrier fluid in this second position.

Figure 10:
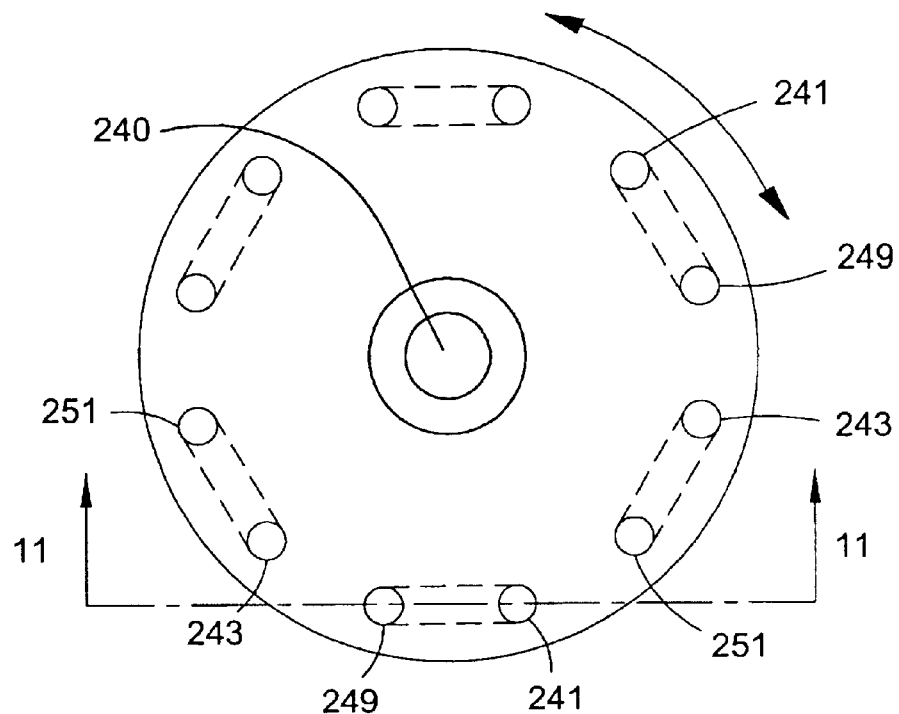
FIG. 10 is a top plan view of the parallel sample injector valve of FIG. 9.
Figure 11:
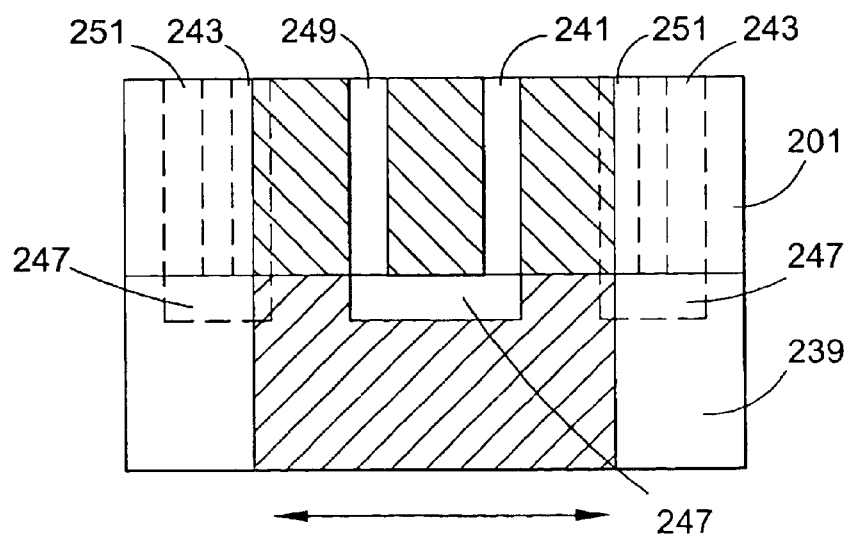
FIG. 11 is a fragmentary section taken along the line 11—11 of FIG. 9 with the sample transfer shuttle in a first position.

A sixth embodiment of a parallel sample injector valve uses rotary motion and includes only a block 201 and a sample transfer shuttle 239, as shown in FIG. 9. The sample transfer shuttle 239 is arranged in a substantial sealing relationship with the block 201. The valve is operated by a rotary actuator (not shown) which operates on a shaft 240. Referring now to FIG. 10, the block 201 includes carrier fluid entry passages 241 and carrier fluid exit passages 249. The block 201 further includes sample entry passages 243 and sample vent passages 251. Referring now to FIG. 11, the sample transfer shuttle 239 includes sample collection chambers 247, which are sized and shaped to define a sample collection volume. In a first position of the sample transfer shuttle 239, the sample collection chambers 247 are substantially in registration with the sample entry passages 243 and sample vent passages 251 of the block 201.

In operation of the sample valve, a volume of sample is allowed to collect in the sample collection chambers 247 in the first position of the sample transfer shuttle 239. The sample transfer shuttle 239 is then moved to a second position by the actuator. In the second position of the sample transfer shuttle 239, the sample collection chambers 247 are substantially in registration with respective ones of the carrier fluid entry passages 241 and the carrier fluid exit passages 249 of the block 201 wherein the volume of sample collected in the sample collection chambers 247 is delivered into the carrier fluid exit passages 249 under pressure of the carrier fluid.

Figure 12:
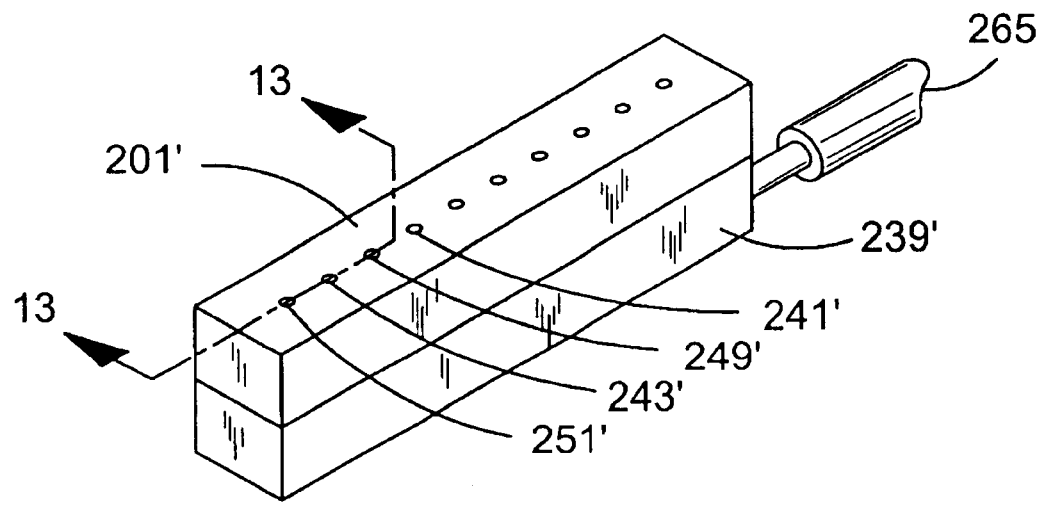
FIG. 12 is a perspective of a seventh embodiment of the parallel sample injector valve.
Figure 13:
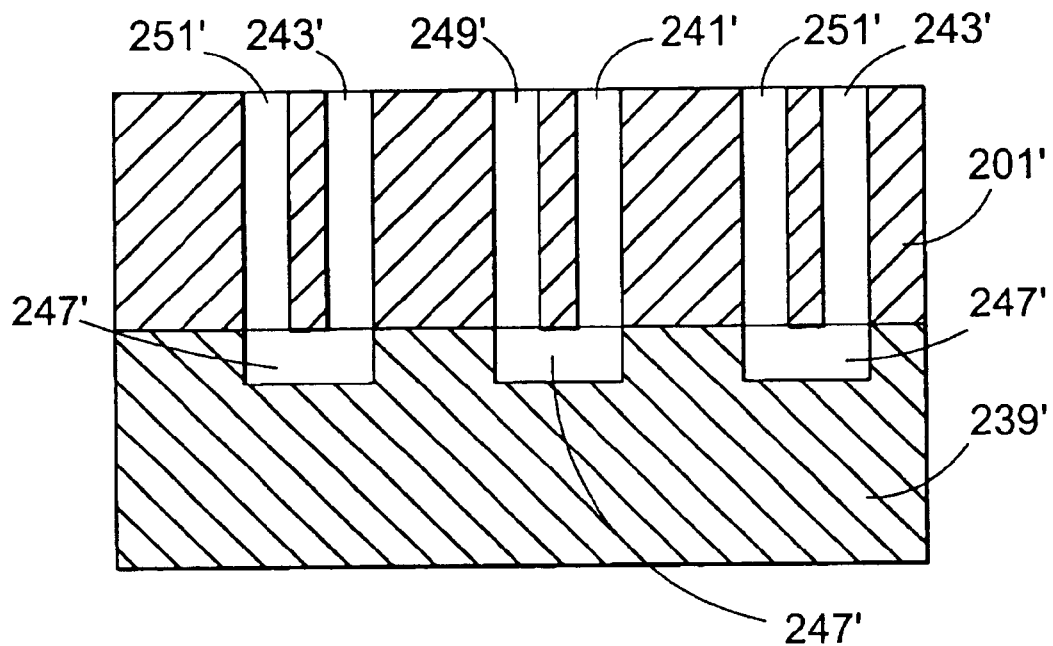
FIG. 13 is a fragmentary section taken along the line 13—13 of FIG. 12 with the sample transfer shuttle in a first position.

A seventh embodiment of the parallel sample injector valve, as shown in FIG. 12, is substantially the same as the sixth embodiment described above except that the sample transfer shuttle 239' operates with linear motion relative to the block 201'. Referring to the figure, the valve comprises a block 201' and a sample transfer shuttle 239'. The sample transfer shuttle 239' is arranged in a substantial sealing relationship with the block 201'. The valve is operated by an actuator 265', which operates on the sample transfer shuttle 239'. The block 201' includes carrier fluid entry passages 241'and carrier fluid exit passages 249'. The block 201' further includes sample entry passages 243' and sample vent passages 251'. Referring now to FIG. 13, the sample transfer shuttle 239' includes sample collection chambers 247', which are sized and shaped to define a sample collection volume. In a first position of the sample transfer shuttle 239', the sample collection chambers 247' are substantially in registration with the sample entry passages 243' and sample vent passages 251' of the block 201'.

In operation of the sample valve, a volume of sample is allowed to collect in the sample collection chambers 247' in the first position of the sample transfer shuttle 239'. The sample transfer shuttle 239' is then moved to a second position by the actuator 265. In the second position of the sample transfer shuttle 239', the sample collection chambers 247' are substantially in registration with respective ones of the carrier fluid entry passages 241' and the carrier fluid exit passages 249' of the block 201' wherein the volume of sample collected in the sample collection chambers 247' is delivered into the carrier fluid exit passages 249' under pressure of the carrier fluid.

Figure 14:
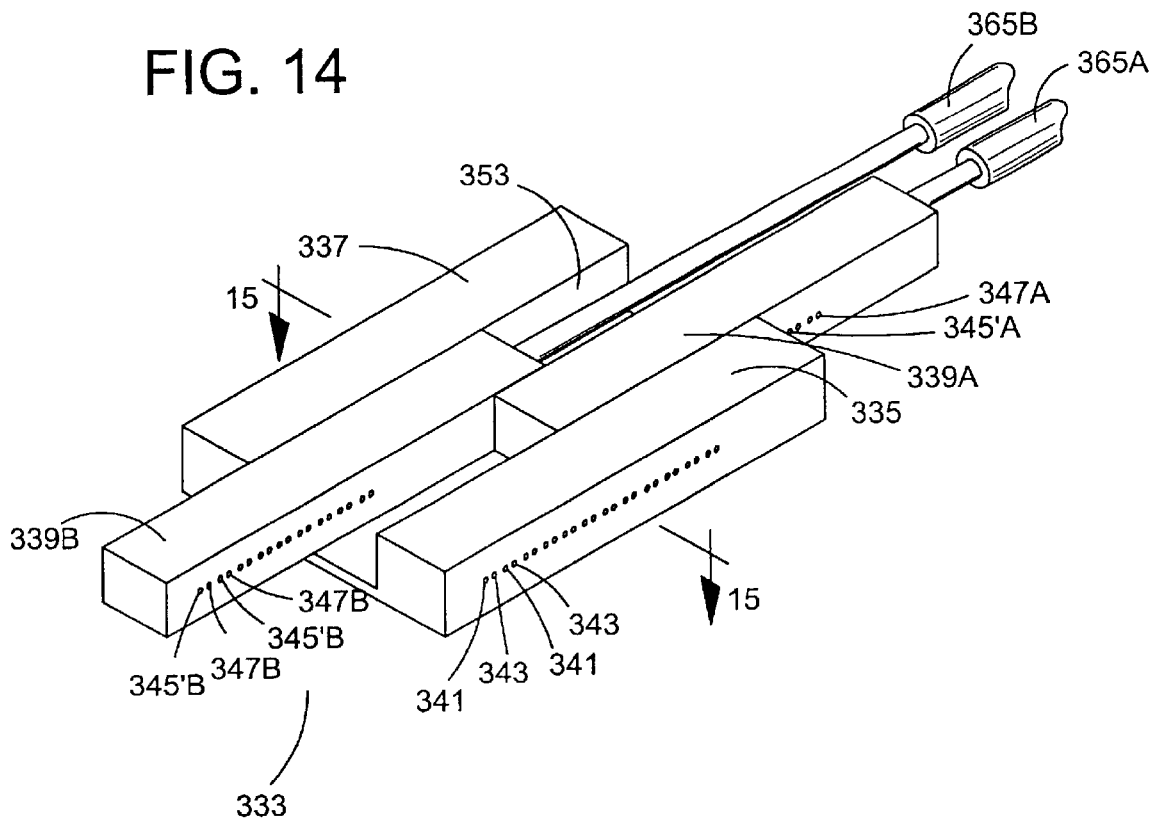
FIG. 14 is a perspective of an eighth embodiment of the present invention incorporating multiple sample transfer shuttles into the valve, the sample transfer shuttles being offset from a normal operating position for purposes of illustration.
Figure 15:
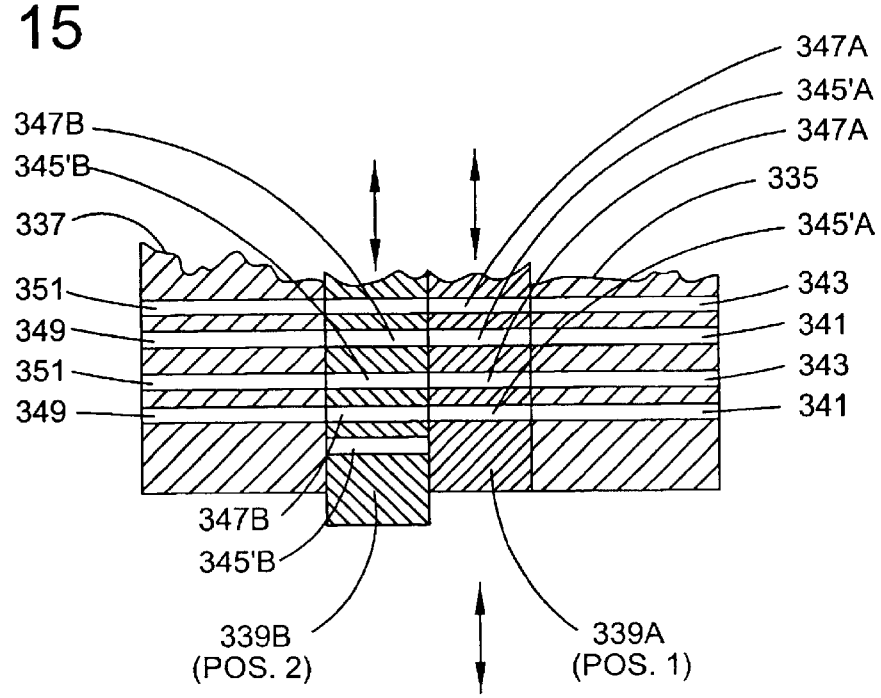
FIG. 15 is a fragmentary section taken along the line 15—15 of FIG. 14 but with one sample transfer shuttles in a first position and another sample transfer shuttle in a second position.

An eighth embodiment of the parallel sample injector valve includes multiple sample transfer shuttles which operate independently. Configuring the valve to include multiple shuttles allows for an increased number of sample throughput combinations while also providing for flexibility in designing sample protocols to include a wider variety of samples and/or sample collection volumes in a shorter period of time. In a combinatorial synthesis application, a multiple shuttle injector valve allows greater flexibility in combining sample and solvent paths. An example of a sample injector valve of the present invention incorporating two independent sample transfer shuttles is shown in FIGS. 14 and 15. While FIG. 14 shows two independently actuated sample transfer shuttles, it is contemplated that more than two sample transfer shuttles may be used in the present invention.

The parallel sample injector valve of FIGS. 14 and 15 comprises a carrier fluid entry block member 335 having carrier fluid entry passages 341 and sample entry passages 343 therein. The valve further comprises a carrier fluid exit block member 337 having carrier fluid exit passages 349 and sample vent passages 351 therein (as shown in FIG. 15). The carrier fluid entry block member 335 and the carrier fluid exit block member 337 are arranged to define a space 353 separating the carrier fluid entry passages 341 of the carrier fluid entry block member 335 from the carrier fluid exit passages 349 of the carrier fluid exit block member 337. Two independent sample transfer shuttles 339A and 339B are slidingly received within the space 353. The sample transfer shuttles have been extended out from their normal operating positions between the carrier fluid entry block member 335 and the carrier fluid exit block member 337 to better illustrate construction of the valve. The sample transfer shuttles 339A and 339B are arranged such that sample transfer shuttle 339A is in substantial sealing relationship with the carrier fluid entry block member 335 and sample transfer shuttle 339B. Sample transfer shuttle 339B is in substantial sealing relationship with the carrier fluid exit block member 337 and sample transfer shuttle 339A. The sample transfer shuttles 339A and 339B each have carrier fluid transfer passages 345A and 345'B and sample collection passages 347A and 347B therein. Each of the sample collection passages 347A and 347B are sized and shaped to define a sample collection volume corresponding to the desired volume of sample to be delivered to the combinatorial chemistry system. Because the sample transfer shuttles 339A and 339B are designed to act independently, the sample collection passages 347A and 347B may be sized and shaped to define either equivalent or different sample collection volumes depending on the particular application and sampling protocol to be employed.

The operation of the sample transfer shuttles 339A and 339B is substantially the same as any of the embodiments as described above. Sample transfer shuttles 339A and 339B are operatively connected to independent actuators 365A and 365B for movement between sample collection and sample delivery positions. Referring now to FIG. 15, in the first position of the sample transfer shuttle 339A, the sample collection passages 347A are in substantial registration with the sample entry passages 343 of the carrier fluid entry block member 335 and the sample vent passages 351 of the carrier fluid exit block member 337. Depending upon the position of the sample transfer shuttle 339B when sample transfer shuttle 9339A is in the first position, the sample collection passages 347A are also in substantial registration with either the carrier fluid transfer passages 345'B or the sample collection passages 347B of sample transfer shuttle 339B.

In operation of the parallel sample injector valve, a volume of sample is allowed to collect in the sample collection passages 347A in the first position of sample transfer shuttle 339A. The sample transfer shuttle 339A is then moved to a second position by the actuator 365A. In the second position of the sample transfer shuttle 339A, the sample collection passages 347A are substantially in registration with respective ones of the carrier fluid entry passages 341 of the carrier fluid entry block member 335 and the carrier fluid exit passages 349 of the carrier fluid exit block member 337. The volume of sample collected in the sample collection passages 347A is delivered into the carrier fluid exit passages 349 under pressure of the carrier fluid. Again, depending upon the position of the sample transfer shuttle 339B when the sample transfer shuttle 339A is in the second position, the sample is delivered under pressure of the carrier fluid into the carrier fluid exit passages 349 by flow through either the carrier fluid transfer passages 345'B or the sample collection passages 347B of sample transfer shuttle 339B.

The operation of the sample transfer shuttle 339B is substantially similar to that of sample transfer shuttle 339A. In the first position of the sample transfer shuttle 339B (not shown), the sample collection passages 347B are in substantial registration with the sample entry passages 343 of the carrier fluid entry block member 335 and the sample vent passages 351 of the carrier fluid exit block member 337. Depending upon the position of the sample transfer shuttle 339A when sample transfer shuttle 339B is in the first position, the sample collection passages 347B are also in substantial registration with either the carrier fluid transfer passages 345'A or the sample collection passages 347A of sample transfer shuttle 339A.

In the first position of sample transfer passage 339B, a volume of sample is allowed to collect in the sample collection passages 347B. The sample transfer shuttle 339B is then moved to a second position by the actuator 365B, as shown in FIG. 15. In the second position of the sample transfer shuttle 339B, the sample collection passages 347B are substantially in registration with respective ones of the carrier fluid entry passages 341 of the carrier fluid entry block member 335 and the carrier fluid exit passages 349 of the carrier fluid exit block member 337. The volume of sample collected in the sample collection passages 347B is delivered into the carrier fluid exit passages 349 under pressure of the carrier fluid. Again, depending upon the position of the sample transfer shuttle 339A when the sample transfer shuttle 339B is in the second position, the carrier fluid flowing to the sample collection passages 347B is flowing through either the carrier fluid transfer passages 345'A or the sample collection passages 347A of sample transfer shuttle 339A. As depicted in FIG. 15, the carrier fluid is flowing through the carrier fluid transfer passages 345'A.

Figure 16:
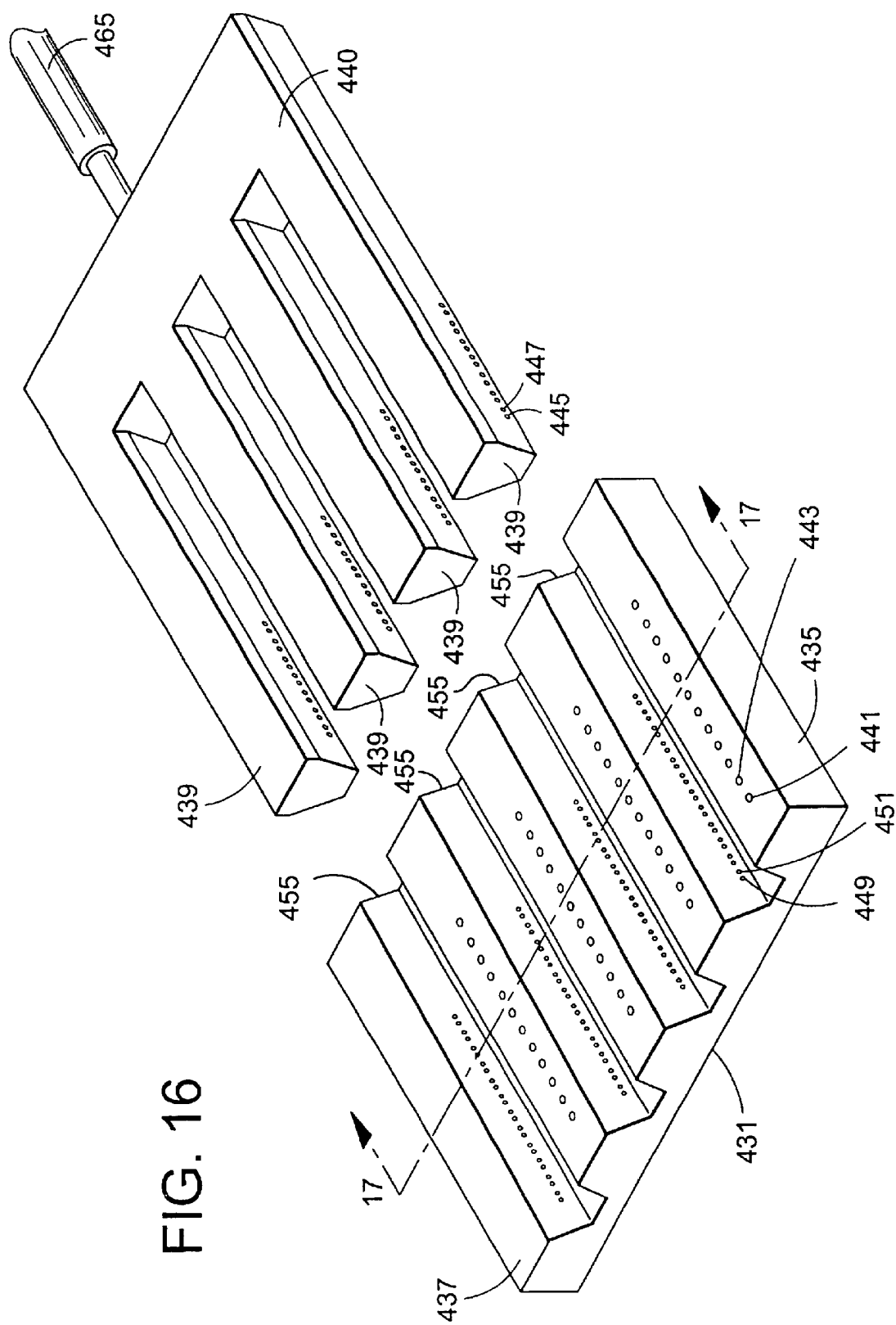
FIG. 16 is an exploded perspective of a ninth embodiment of the present invention wherein multiple sample transfer shuttles are operated by one actuator.
Figure 17:
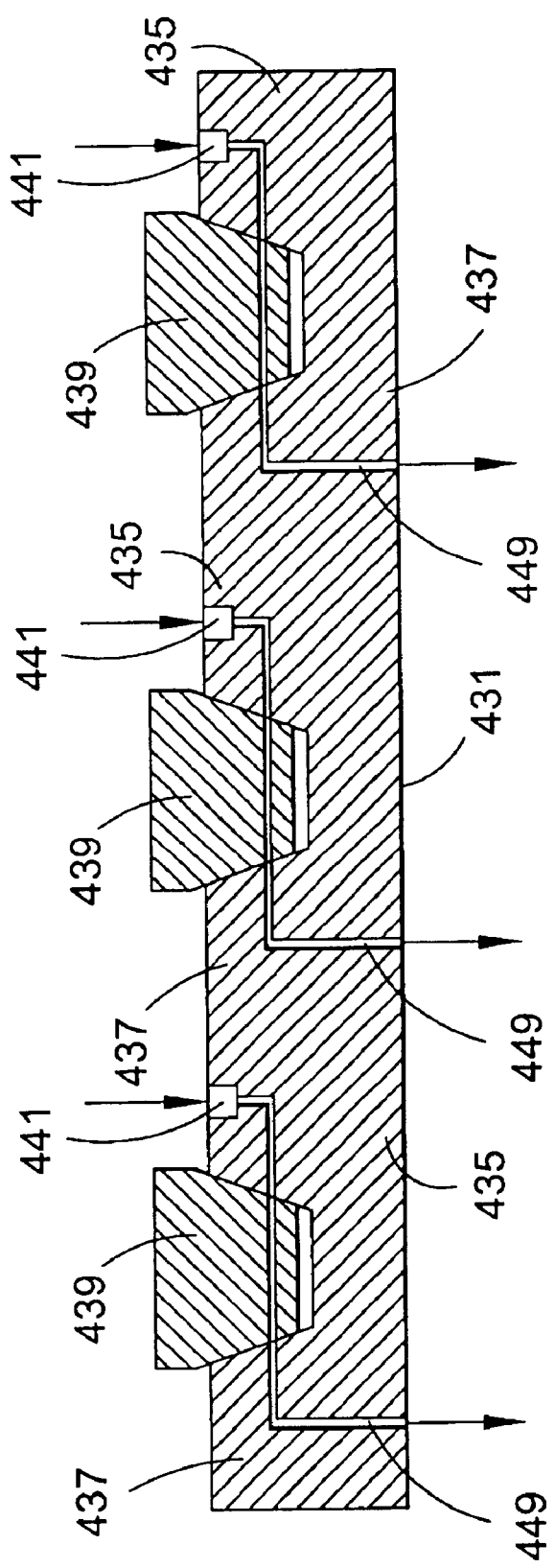
FIG. 17 is a vertical cross section taken along the line 17—17 of FIG. 16 but showing the sample transfer shuttles of the valve in the block.

A ninth embodiment incorporates a combination of multiple individual sample valves into a single valve. Such a configuration allows the valves to be planarized to more easily mate the sample entry ports with automatic sampling equipment and to allow for injecting more samples in a smaller space. One such example is a "comb" shuttle configuration as shown in FIGS. 16 and 17. Multiple carrier fluid entry block members 435 and carrier fluid exit block members 437 are formed as a monolithic valve 431. The carrier fluid entry block members 435 have carrier fluid entry passages 441 and sample entry passages 443 therein. The carrier fluid exit block members 437 include carrier fluid exit passages 449 and sample vent passages 451. The blocks are arranged to define channels 455 spacing apart the carrier fluid entry passages 441 of the carrier fluid entry block members 435 from the carrier fluid exit passages 449 of the carrier fluid exit block members 437. Referring briefly to FIG. 17, it is important to note that the carrier fluid entry passages 441 and carrier fluid exit passages 449 as well as the sample entry passages 443 and sample vent passages 451 are arranged on the top and the bottom of the carrier fluid entry block members 435 and carrier fluid exit block members 437 respectively to accommodate the arrangement of block members in the monolithic valve 431. Because the carrier fluid entry block members 435 and carrier fluid exit block members 437 are arranged side to side in the monolithic valve, the ports for carrier fluid entry 441 and sample entry 443 and the ports for carrier fluid exit 449 and sample vent 451 are configured vertically, being located on the top and bottom of the carrier fluid entry block members 435 and carrier fluid exit block members 437 as shown in FIG. 17.

The valve further includes a sample transfer shuttle assembly 440 comprising multiple sample transfer shuttles 439. Each of the sample transfer shuttles 439 of the sample transfer shuttle assembly 440 have carrier fluid transfer passages 445 and sample collection passages 447 therein. The sample transfer shuttle assembly 440 is sized and shaped such that the sample transfer shuttles 439 are arranged to comprise the "teeth" of a "comb." Each of the sample transfer shuttles 439 is slidingly received in a respective one of the channels 453 in substantially sealing relationship to the carrier fluid entry block members 435 and carrier fluid exit block members 437.

The operation of the sample injector valve is substantially the same as the first embodiment. The sample injector valve operates by moving the sample transfer shuttle 439 between a first position and a second position. The sample transfer shuttle assembly 440 is moved by an actuator 465 operatively connected to the solid end of the sample transfer shuttle assembly 440. In the first position of the sample transfer shuttle assembly 440, the sample collection passages 447 of the individual sample transfer shuttles 439 are substantially in registration with respective ones of the sample entry passages 443 of the carrier fluid entry block members 435 and sample vent passages 451 of the carrier fluid exit block members 437. The carrier fluid transfer passages 445 are in substantial registration with respective ones of the carrier fluid entry passages 441 of the carrier fluid entry block members 435 and carrier fluid exit passages 449 of the carrier fluid exit block members 437.

In the first position of the sample transfer shuttle assembly 440, a volume of sample is allowed to collect in the sample collection passages 447. The sample transfer shuttle assembly 440 is then moved to a second position by the actuator 465. In the second position of the sample transfer shuttle assembly 440, the sample collection passages 447 of the individual sample transfer shuttles 439 are substantially in registration with respective ones of the carrier fluid entry passages 441 and carrier fluid exit passages 449 of the carrier fluid entry block members 435 and carrier fluid exit block members 437. The volume of collected sample in the sample collection passages 447 is delivered into the carrier fluid exit passages 449 under pressure of the carrier fluid.

It is contemplated that all of the above embodiments may be combined as modular components in a larger valve apparatus. For example, any of the embodiments can be arranged side by side to create a larger parallel valve apparatus comprising a two dimensional array of individual parallel sample injector valves of the present invention. Further, it is contemplated that the present invention may comprise a combination of either 12 individual sample injector valves accommodating 8 parallel sample ports each or 8 individual sample injector valves accommodating 12 parallel sample ports sized and shaped to accommodate samples from a standard 96-well microtiter plate. An example of a two dimensional array 531 of parallel sample injector valves with such a microtiter plate 533 is illustrated in FIGS. 18A and 18B. Operation of each of the sample injector valves of the two dimensional array 531 is as described for the first embodiment above with each of the individual sample injector valves including a carrier fluid entry block member 535 having carrier fluid entry passages 541 and sample entry passages 543 therein, a sample transfer shuttle 539 having carrier fluid transfer passages 545 and sample collection passages 547 therein, and a carrier fluid exit block member 537 having carrier fluid exit passages 549 and sample vent passages 551 therein. The operation of the individual valves of the two-dimensional array 531 is substantially the same as the first embodiment described above wherein each sample transfer shuttle 539 is moved between a first and second position by respective actuator 565.

Figure 19B:
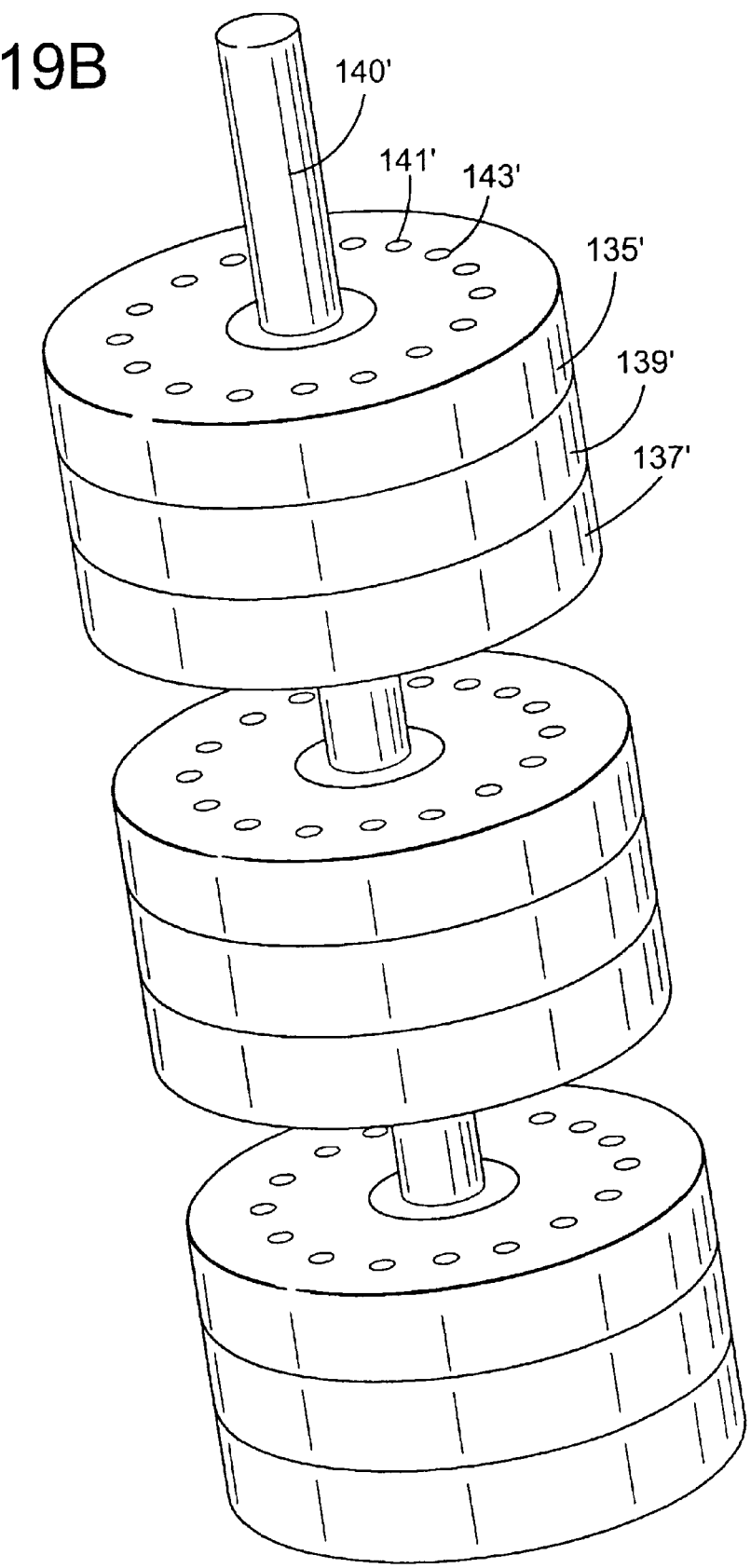
FIG. 19A is a vertical cross section similar to FIG. 18A of an embodiment of the present invention incorporating multiple separate parallel sample injector valves into a three dimensional array; and, FIG. 19B is a perspective of a rotary embodiment of the present invention incorporating multiple separate parallel sample injector valves into a three dimensional array.

The number of samples and streams of fluid in the valves of the present invention can also be increased by stacking as illustrated in FIGS. 19A and 19B. Referring to FIG. 19A, operation of the valve is as described for the first embodiment above. Operation of each of the sample injector valves in the stack operates as described for the first embodiment above with each of the individual sample injector valves including a carrier fluid entry block member 535' having carrier fluid entry passages 541' and sample entry passages (not shown) therein, a sample transfer shuttle 539' having carrier fluid transfer passages 545' and sample collection passages (not shown) therein, and a carrier fluid exit block member 537' having carrier fluid exit passages 549' and sample vent passages (not shown) therein. Referring to FIG. 19B, the rotary valves of the present invention may also be stacked. Operation of each of the rotary sample injector valves is as described for the fifth embodiment above (FIG. 7) with each of the individual sample injector valves including a shaft 140', a carrier fluid entry block member 135' having carrier fluid entry passages 141' and sample entry passages 143' therein, a sample transfer shuttle 139' having carrier fluid transfer passages (not shown) and sample collection passages (not shown) therein, and a carrier fluid exit block member 137' having carrier fluid exit passages (not shown) and sample vent passages (not shown) therein. Such three dimensional arrangements increase the packing factor of the valve arrangement and allows for more samples in compact spacing.

When intarodicing elements of the present invention or "the" and "said" are intended to mean that there are one, or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense. In view of the above, it will be seen that the several objects of the invention are achieved and other advantageous results attained.

What is claimed is:

1. A sample injector valve for use in injecting samples of material into a combinatorial chemistry system, the sample injector valve comprising:

a block and a shuttle, the block having carrier fluid entry passages and carrier fluid exit passages therein, the carrier fluid entry passages being adapted for connection to a source of pressurized carrier fluid for urging carrier fluid to flow through the valve, and further comprising sample entry passages and sample vent passages, the shuttle being slidingly received in substantially sealing relationship with the block, the shuttle having transfer passages therein having sample collection volumes;

one actuator operatively connected to the shuttle for moving the shuttle in the valve between a first position in which samples of material to be analyzed can be collected in the shuttle and a second position in which multiple collected samples can be fed into said carrier fluid exit passages for delivery to the combinatorial chemistry system, in the first position at least some of the transfer passages of the shuttle being substantially in registration with respective ones of the sample entry passages and sample vent passages for receiving a volume of sample material substantially equal to the sample collection volume of the transfer passage, in the second position at least some of the transfer passages being substantially in registration with respective ones of said carrier fluid entry and exit passages for substantially simultaneous delivery of the multiple collected samples in the transfer passages into said carrier fluid exit passages under pressure of the carrier fluid.

2. A sample injector valve as set forth in claim 1 wherein the shuttle further includes flow through passages arranged for substantial registration with respective ones of the carrier fluid entry and exit passages in the first position whereby carrier fluid flow to the combinatorial chemistry system may be maintained during sample collection.

3. A sample injector valve as set forth in claim 2 wherein others of the shuttle transfer passages are arranged for substantial registration with respective ones of said sample entry and sample vent passages in the second position of the sample transfer shuttle, said other transfer passages being sized and shaped to collect a volume of sample in said second position; the other shuttle transfer passages being arranged for substantial registration with said carrier fluid entry and exit passages in the first position of the sample transfer shuttle for delivery of the volume of collected sample in the transfer passage into said carrier fluid exit passage under pressure of the carrier fluid.

4. A sample injector valve as set forth in claim 1 wherein the block comprises first and second block members.

5. A sample injector valve as set forth in claim 4 wherein the carrier fluid entry passages and the sample entry passages are in the first of the block members and the carrier fluid exit passages and sample vent passages are in the second block member.

6. A sample injector valve as set forth in claim 5 wherein the first and second block members are at least partially in opposing relationship defining a space there between, and the shuttle is disposed in the space in sealing, sliding relationship with the first and second block members.

7. A sample injector valve as set forth in claim 6 wherein the shuttle is adapted for linear motion relative to the first and second block members.

8. A sample injector valve as set forth in claim 7 wherein the first and second block members are formed as a single piece block, and wherein the space between the first and second block members comprises a channel formed in the single piece block.

9. A sample injector valve as set forth in claim 8 wherein said single piece block further includes carrier fluid bypass passages in fluid communication with said carrier fluid entry and exit passages whereby a substantially constant fluid pressure may be maintained in the carrier exit passage.

10. A sample injector valve as set forth in claim 1 wherein the block further includes a chamber in fluid communication with said carrier fluid exit passages, said chamber having a pressure regulation mechanism such that carrier exit fluid is allowed to accumulate in said chamber during normal flow of carrier fluid through the sample injector valve, and carrier exit fluid is pushed out of the accumulation chamber by the pressure regulation mechanism when a decrease in carrier fluid pressure occurs in the carrier fluid exit passage, whereby a substantially constant fluid pressure may be maintained in the carrier fluid exit passage.

11. A sample injector valve as set forth in claim 10 wherein the pressure regulation mechanism comprises a spring or a compressible fluid operating on a bladder.

12. A sample injector valve as set forth in claim 1 wherein the shuttle is adapted for rotary motion relative to the block.

13. A sample injector valve as set forth in claim 12 wherein the block comprises first and second block members wherein the shuttle is sandwiched between the first and second block members.

14. A sample injector valve as set forth in claim 1 comprising multiple blocks and multiple shuttles.

15. A sample injector valve as set forth in claim 14 wherein at least two of said blocks, each receiving at least one of said shuttles, are stacked on top of at least two more of said blocks, each receiving at least one of said shuttles, to create planar arrays of sample entry passages.

16. A sample injector valve as set forth in claim 14 wherein said multiple blocks and multiple shuttles are arranged in a two dimensional array.

17. A sample injector valve as set forth in claim 16 wherein said two dimensional array of multiple blocks and multiple shuttles is constructed to simultaneously accommodate samples from a standard 96-well microtiter plate.

18. A sample injector valve as set forth in claim 17 wherein said two dimensional array comprises 12 individual sample injector valves accommodating 8 parallel sample ports each.

19. A sample injector valve as set forth in claim 17 wherein said two dimensional array comprises 12 individual sample injector valves accommodating 12 parallel sample ports each.

20. A sample injector valve as set forth in claim 14 wherein at least one of said shuttles is adapted for rotary motion relative to at least one of said blocks.

21. A sample injector valve as set forth in claim 1 wherein said valve further comprises at least two sample transfer shuttles and at least two actuators, said actuators being operable to independently actuate a corresponding one of said sample transfer shuttles.

22. A sample injector valve as set forth in claim 1 wherein said valve further comprises at least two sample transfer shuttles operated by the actuator.

23. A sample injector valve as set forth in claim 22 wherein said sample transfer shuttles are formed as one piece, including a connecting member interconnecting the shuttles, each shuttle projecting outwardly from the connecting member generally parallel to the other sample transfer shuttles.

24. A sample injector valve as set forth in claim 1 wherein the sample entry passages each have an entry port spaced along the block a distance selected for mating with an automatic sample feeder having plural sample injection devices.

25. A sample injector valve as set forth in claim 24 in combination with the automatic sample feeder and a combinatorial chemistry system, said carrier fluid exit passages being connected in fluid communication with the combinatorial chemistry system.

26. The combination as set forth in claim 25 wherein the combinatorial chemistry system is high pressure liquid chromatography for the evaluation of a combinatorial library.

27. The combination as set forth in claim 26 further in combination with an automated sample loading robot.

28. A sample injector valve as set forth in claim 1 wherein said block comprises from about 8 to about 12 sample entry passages.

* * * * *

UNITED STATES PATENT AND TRADEMARK OFFICE
CERTIFICATE OF CORRECTION

PATENT NO.     : 6,632,404 B1
DATED          : October 14, 2003
INVENTOR(S)    : J. Christopher Freitag et al.

It is certified that error appears in the above-identified patent and that said Letters Patent is hereby corrected as shown below:

Column 15,
Line 38, "12 individual" should read -- 8 individual --.

Signed and Sealed this

Tenth Day of February, 2004

JON W. DUDAS
*Acting Director of the United States Patent and Trademark Office*